(12) United States Patent
Goedeke et al.

(10) Patent No.: US 6,263,246 B1
(45) Date of Patent: Jul. 17, 2001

(54) METHOD AND APPARATUS FOR COMMUNICATIONS WITH AN IMPLANTABLE DEVICE

(75) Inventors: Steven D. Goedeke, Forest Lake; Charles H. Dudding, Lino Lakes, both of MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/395,925

(22) Filed: Sep. 14, 1999

(51) Int. Cl.$^7$ ..................................... A61N 1/08
(52) U.S. Cl. ................................. 607/60; 607/30
(58) Field of Search ................... 607/2, 30, 32, 607/59, 60, 3; 600/300, 301, 523, 522

(56) References Cited

U.S. PATENT DOCUMENTS

| | | |
|---|---|---|
| 4,146,029 | 3/1979 | Ellinwood, Jr. . |
| 4,601,291 | 7/1986 | Boute et al. . |
| 4,692,147 | 9/1987 | Duggan . |
| 5,107,833 | 4/1992 | Barsness . |
| 5,113,869 | 5/1992 | Nappolz et al. . |
| 5,331,966 | 7/1994 | Bennett et al. . |
| 5,342,408 | 8/1994 | DeCoriolis et al. . |
| 5,342,409 | 8/1994 | Mullett . |
| 5,354,319 | 10/1994 | Wyborney et al. . |
| 5,357,427 | * 10/1994 | Langen et al. ............ 600/300 |
| 5,372,607 | 12/1994 | Stone et al. . |
| 5,383,909 | 1/1995 | Keimel . |
| 5,433,736 | * 7/1995 | Nilsson ........................ 607/59 |
| 5,456,692 | 10/1995 | Smith, Jr. et al. . |
| 5,662,689 | 9/1997 | Elsberry et al. . |
| 5,693,076 | 12/1997 | Kaemmerer . |
| 5,752,977 | 5/1998 | Grevious et al. . |
| 5,843,138 | 12/1998 | Evers et al. . |
| 5,843,139 | 12/1998 | Goedeke et al. . |

OTHER PUBLICATIONS

U.S. application No. 09/302,932, filed Apr. 30, 1999 by Villaseca, entitled "Telemetry System for Implantable Medical Devices".
U.S. application No. 09/302,637, filed Apr. 30, 1999 by Goedeke entitled "Telemetry System for Implantable Medical Devices".

* cited by examiner

Primary Examiner—Kennedy Schaetzle
(74) Attorney, Agent, or Firm—Girma Wolde-Michael; Beth L. McMahon

(57) ABSTRACT

An implantable medical device and a method of operation thereof. The implantable device includes apparatus for delivering a therapy to a patient or monitoring a physiologic parameter of a patient and control circuitry for modifying operation of the device. The device further includes an audio receiver responsive to sequences of DTMF tones and coupled to the control circuitry, which modifies the operation of the device responsive to received DTMF tone sequences. The device preferably includes a telemetry system and the control circuitry may modify operation of the telemetry system responsive to received DTMF tone sequences. In addition or alternatively, the control circuitry may modify operation of the apparatus for delivering a therapy to a patient or monitoring a physiologic parameter responsive to received DTMF tone sequences. The device may further include an audio tone generator for generating a tone or series of tones indicative of operation or status of the device.

8 Claims, 1 Drawing Sheet

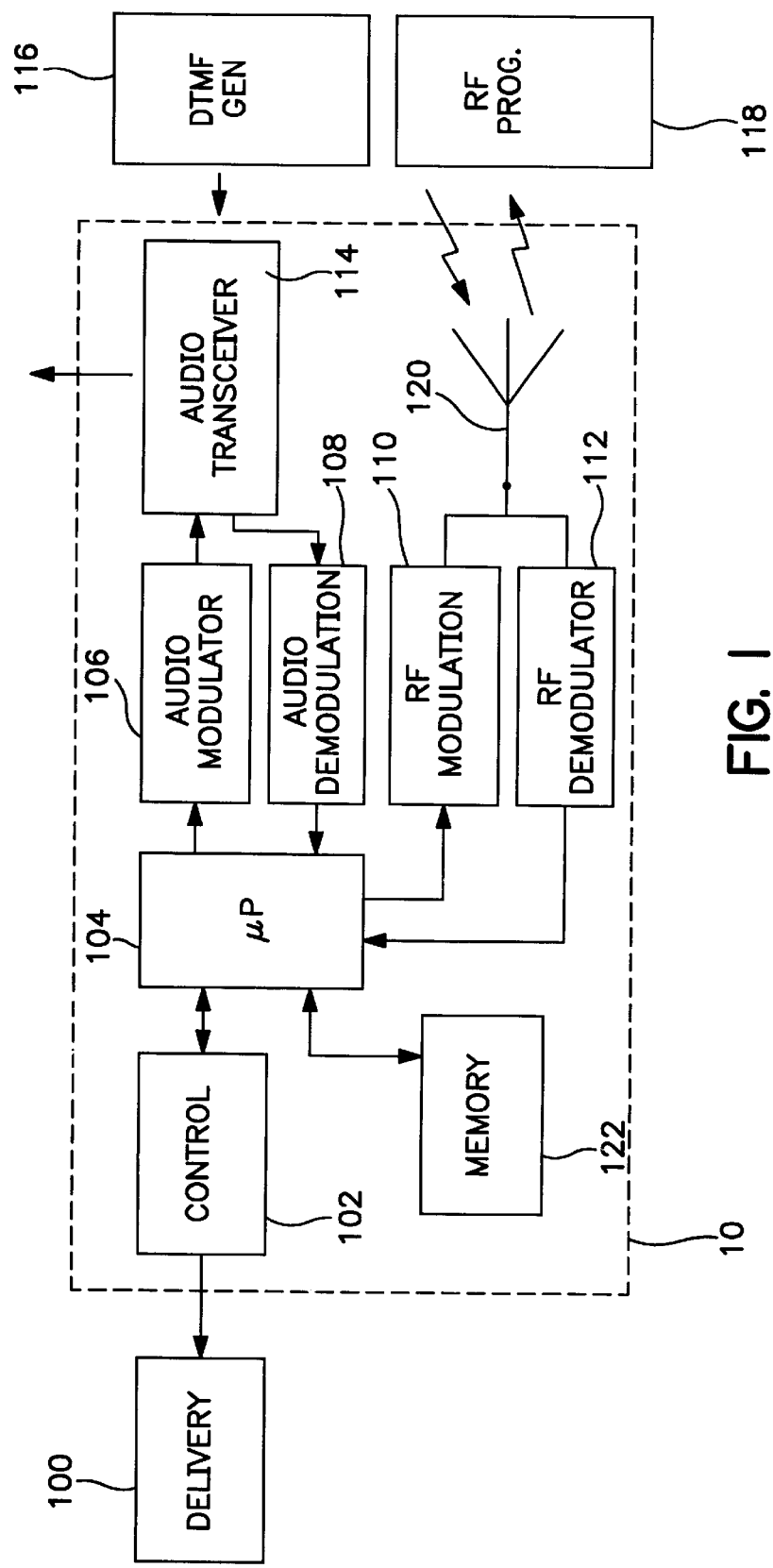

METHOD AND APPARATUS FOR COMMUNICATIONS WITH AN IMPLANTABLE DEVICE

BACKGROUND OF THE INVENTION

This invention relates generally to diagnostic and therapeutic devices for implant in a patient's body, and more particularly to devices that monitor physiologic parameters and/or provide corrective therapies in conjunction with external monitoring and/or programming devices.

A wide variety of implantable devices have been developed for use in the human body to monitor the patient's condition and/or to treat a patients underlying disease state. Of these, implantable pacemakers are probably the most widely known, but also available are implantable defibrillators, implantable drug delivery devices, implantable nerve and muscle stimulators and a variety of implantable monitors. Most of these devices are used in conjunction with external monitoring and/or programming devices that control the operation of the implanted devices and receive information from the implantable devices. Examples of programmable implantable pacemakers include U.S. Pat. No. 5,456,692, issued to Smith et al., U.S. Pat. No. 5,843,138, issued to Evers, U.S. Pat. No. 5,372,607, issued to Stone et al., U.S. Pat. No. 5,843,139, issued to Goedeke et al., U.S. Pat. No. 4,601,291, issued to Boute et al., U.S. Pat. No. 5,693,076, issued to Kaemmerer, et al., U.S. Pat. No. 5,752,977, issued to Grevious et al., U.S. Pat. No. 5,354,319 issued to Wyborny et al. and U.S. Pat. No. 5,107,833, issued to Barsness et al., all incorporated herein in their entireties. Examples of the various other types of programmable implantable devices listed above include U.S. Pat. No. 5,342,408, issued to DeCoriolis et al., U.S. Pat. No. 5,383,909, issued to Keimel, U.S. Pat. No. 4,146,029, issued to Ellinwood, U.S. Pat. No. 4,692,147, issued to Dugan, U.S. Pat. No. 5,662,689, issued to Ellsberry et al, U.S. Pat. No. 5,342,409, issued to Mullett and U.S. Pat. No. 5,331,966, issued to Bennett et al., all incorporated herein in their entireties.

In many of the devices described above, activation of telemetry from the implanted device to the associated external device requires placement of a magnet in physical proximity to the device. The same type of magnet may also activate a temporary change in device operation. The best-known example of such an operational mode change is the initiation of asynchronous pacing operation in an implantable pacemaker, enabling the patient or the patient's physician to conveniently determine the present pacing rate. This type of magnetically triggered mode change is also useful in the context of trans-telephonic pacemaker monitoring, allowing the remote monitoring device to record a paced electrogram, if desired.

The requirement of magnetic activation of the device's telemetry function or mode change, while serving as a useful safety feature, does have some drawbacks. First, the magnets employed are typically relatively heavy, high power magnets of a type not typically available other than from the device manufacturer, making them inconvenient and expensive to replace in the event they are lost or broken. This does not pose a problem in the context of programming or monitoring the implanted device using a programmer which employs a programming head placed in proximity to the patient's body, as such programming heads typically include a built-in magnet, typically a permanent magnet. However, as programming systems which employ programming antennas which may be remote from the body are developed, for example as disclosed in U.S. Pat. No. 5,113,869, issued to Nappholz et al., U.S. patent application Ser. No. 09/302,932, filed on Apr. 30, 1999 by Villaseca et al., for a "Telemetry System for Implantable Medical Devices", U.S. patent application Ser. No. 09/302,637, filed on Apr. 30, 1999 by Goedeke, for a "Telemetry System for Implantable Medical Devices", all incorporated herein in their entireties, a magnet within the programmer is not workable. Second, placement of the magnet in proper orientation and location with regard to the implanted device is sometimes difficult, making the process more cumbersome than might be desirable.

SUMMARY OF THE INVENTION

The present invention is directed toward providing a mechanism that, in the context of an implantable device, provides the functions typically provided by a magnet and an associated magnetic switch and circuitry within an implantable medical device that overcomes problems as described above. An implantable device according to the present invention is provided with an audio receiver such as a microphone and internal associated circuitry capable of demodulating DTMF tones of the type employed in modem touch-tone telephones. In response to a defined sequence of DTMF tones, the device may initiate telemetry transmission or exhibit a change in the operational mode of the device, as previously accomplished by means of an applied magnet. The device employed to deliver the DTMF tone sequence may be similar to an auto-dialer, of the type available at electronics stores, pre-programmed with one or more sequences of tones. Alternatively, or if the physician provided device is lost or broken, an off the shelf auto-dialer may be employed, with one or more memorized numbers used to activate the device telemetry or to trigger a change in operating mode. Alternatively, the patient's own touch-tone phone preferably a phone with the capability to memorize several phone numbers might be employed.

Because the DTMF tone-generating device (e.g. an auto-dialer) can store multiple sequences of tones, it may be employed to control multiple operational parameters and/or activate device telemetry independently of mode changes, a benefit not typically available using a simple magnet. As an added benefit, the DTMF tone generating device may also have the patient's physician's phone number memorized and may also be used to assist in contacting the physician.

In preferred embodiments of the invention, the implanted device also includes a mechanism for generating audible feedback to indicate to the patient and/or physician that the DTMF tones have been received. For example, the microphone within the device may also serve as a speaker and may be driven by associated audio modulation circuitry within the device. The audio feedback may include differing series of tones, depending on the information to be conveyed.

BRIEF DESCRIPTION OF THE DRAWING

FIG. 1 is a functional block diagram of a device according to a preferred embodiment of the present invention.

DETAILED DESCRIPTION OF THE PREFERRED EMBODIMENTS

FIG. 1 illustrates a first embodiment of the invention. The implanted device 10 includes a mechanism 102 for controlling one or more operations of the device, which may include provision of one, or more desired therapies and/or monitoring one or more physiologic parameters within the patient, coupled to a mechanism 100 for delivering the desired therapies and/or sensing the physiologic parameters to be monitored. In the context of devices as discussed above, the controlling mechanism 102 might be a cardiac pacemaker or defibrillator, capable of generating cardiac pacing and/or pulses and responding to depolarizations of one or more chambers of a patient's heart, while the delivery mechanism 100 might be one or more electrodes, capable of stimulation heart tissue and receiving electrical signals indicative of heart depolarizations and optionally may include one or more additional physiologic sensors. Alternatively, control mechanism 102 might be a drug pump, with delivery mechanism 100 taking the form of a delivery catheter and optionally may include one or more additional physiologic sensors. Corresponding alternative configurations of the implanted device might include corresponding control and delivery apparatus appropriate to implantable monitors, nerve stimulators or the like, as is typical of such devices.

The implantable device 10 preferably operates under control of a microprocessor 104, which provides supervisory control of all components of the implanted device 10. The device 10 further preferably includes a memory 122 that stores information relative to operational parameters of the device and relative to physiologic parameters sensed by the device. The contents of memory 122 include information to be telemetered to an associated external programmer/monitor 118 and information received from the associated external programmer/monitor 118 indicative of the desired operational mode of the device 10.

External programmer/monitor 118 communicates with the implanted device in the illustrated embodiment by means of an RF link, as is conventional in the context of implanted device programmers. The implanted device 10 includes an antenna 120 coupled to RF modulation circuitry 110 and RF demodulation circuitry 112 for transmitting information to and receiving information from external programmer/monitor 118. The antenna and associated modulation and demodulation circuitry may correspond to any of those described in the patents discussed above. However, the invention is believed particularly beneficial in the context of devices which are adapted to communicate with programmers/monitors located remote from the patient as described in the Villaseca et al. and Goedeke patent applications and the Nappholz patent discussed above.

The device 10 is also provided with an audio transceiver 114 which may take the form of a microphone/speaker, for example, a piezo-electric transducer, which is coupled to associated audio modulation and demodulation circuitry 106 and 108. Modulation and demodulation circuitry 106 and 108 may correspond to any known circuitry employed to create and decode DTMF tones as employed by touch-tone telephony. For example, demodulation circuitry 108 may correspond to commercially available DTMF decoder chips as manufactured by Motorola, Inc. and others and modulation circuitry 106 may correspond to DTMF tone generator circuits as employed in modem touch-tone telephones. Modulation circuitry may alternatively or in addition generate audio signals other than DTMF tones. DTMF tone sequence generator 116 may be a device such as an auto-dialer, having the capability of generating desired sequences of DTMF tones, preferably in response to the push of a single button.

The DTMF tone generator 116 may be employed, for example, as part of a programming or follow-up procedure, in conjunction with a programmer/monitor 118 which does not need to be in close proximity to the patient. In such case, the patient may be seated at a distance of several feet from the programmer/monitor 118, the physician may activate the programmer/monitor 118 and the patient may employ the DTMF tone generator to activate the RF telemetry of the implanted device 10. Either following successful activation of the implanted device's telemetry of following successful establishment of reliable communication between the device 10 and programmer/monitor 118, the audio transceiver 114 may optionally be activated to generate a DTMF tone or other tone or a series of DTMF tones or other tones so indicating. In some embodiments of the invention, the audio transceiver 114 may additionally be employed to provide tones indicative of other aspects of the operation or status of the implanted device, which tones may also be received and demodulated by an audio receiver in a programmer or monitor associated with the device.

The DTMF tone generator may also be employed to change the operational mode of the device 10. For example, if device 10 is a cardiac pacemaker, DTMF tone generator 116 may be employed to cause the device 10 to operate in an asynchronous mode to allow the patient or physician to determine the pacemaker's present rate by taking the patient's pulse rate. Similarly, the DTMF generator may be employed in conjunction with electrogram monitoring equipment, either in the physician's office or trans-telephonic, in order to facilitate recording of a paced electrogram.

The preceding discussion of the use of the DTMF tone generator describes its use as stand-alone apparatus. However, it should also be understood that in cases in which a programmer or monitor is provided which employs a programming head intended for use closely adjacent the implanted device, a DTMF tone generator will of course also be included in the programming head.

Recently, particularly in conjunction with implanted neurostimulators and implanted atrial defibrillators, it has become common to provide the patient with a limited function programmer/monitor. In the context of implanted neurostimulators, the patient's programmer typically provides the patient with the ability to adjust the amplitude of the neurostimulation pulses and to disable the device. In the context of implanted atrial defibrillators, the patient's programmer typically provides the patient with the ability to trigger or override the deliver of atrial defibrillation pulses. In conjunction with these types of devices, a DTMF tone generator 116 may be employed with such a patient programmer 118 or incorporated within such a patient programmer 118 to enable telemetry transmission from the implanted device.

As an added benefit, in some embodiments of the invention, particularly in cases where it is desirable that the patient has a limited capability to program the implanted device, the DTMF tone generator 116 may serve as an alternate mechanism for permanently modifying the operational parameters of the implanted device 10 or triggering therapy. For example, in the case in which the DTMF tone generator takes the form of an auto-dialer, and the implanted device 10 takes the form of an implanted pacemaker/atrial defibrillator, the DTMF generator 116 may store tone sequences which will activate the implanted device's telemetry system, switch the operation of the pacemaker portion of the device to asynchronous mode, reduce the pacing rate at night to assist sleep and/or disable, override or trigger atrial defibrillation therapies, eliminating the necessity of a more expensive RF type patient programmer 118 entirely. In this case, if the DTMF tone generator 118 provided by the physician is lost or broken, it may also be readily replaced at little cost to the patient. In a pinch, the patient may even employ his or her touch tone phone to manually generate the tone sequences to affect the desired operational changes, preferably while in telephone communication with the physician.

In conjunction with the above specification, We claim:

1. In an implantable medical device including means for delivering a therapy to a patient or monitoring a physiologic parameter of a patient and control means for modifying operation of the device, the improvement wherein:

the device comprises an audio receiver responsive to sequences of DTMF tones and coupled to the control means and wherein the control means modifies the operation of the device responsive to received DTMF tone sequences.

2. The device of claim 1 wherein the device includes a telemetry system and wherein the control means modifies operation of the telemetry system responsive to received DTMF tone sequences.

3. The device of claim 1 wherein the control means modifies operation of the means for delivering a therapy to a patient or monitoring a physiologic parameter responsive to received DTMF tone sequences.

4. The device of claim 1 further comprising an audio tone generating means for generating a tone or series of tones indicative of operation or status of the device.

5. A method of controlling an implantable medical device including means for delivering a therapy to a patient or monitoring a physiologic parameter of a patient and including an audio receiver within the device, comprising:

receiving a sequence of DTMF tones using the audio receiver and modifying the operation of the device responsive to received DTMF tone sequences.

6. The method of claim 5 wherein the device further includes a telemetry system and wherein modifying the operation of the device comprises modifying operation of the telemetry system responsive to received DTMF tone sequences.

7. The method of claim 5 wherein modifying the operation of the device comprises modifying operation of the means for delivering a therapy to a patient or monitoring a physiologic parameter responsive to received DTMF tone sequences.

8. The method of claim 5 wherein the device comprises an audio tone generator, further comprising generating an audio tone or series of tones indicative of operation or status of the device.

* * * * *